United States Patent [19]

Chapus et al.

[11] Patent Number: Plant 6,387

[45] Date of Patent: Nov. 8, 1988

[54] PEACH TREE NAMED STARCREST

[75] Inventors: Paul Chapus, St.-Laurent-du-Pape; Hubert Veauvy, Crest, both of France

[73] Assignee: G.I.E. Star Fruits, Vedene, France

[21] Appl. No.: 2,041

[22] Filed: Jan. 12, 1987

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Townsend and Townsend

[57] ABSTRACT

A new and distinct variety of peach tree, varietal name Starcrest, is a branch mutation of a Springcrest peach. The new variety is characterized by its bright red blush or striped red on yellow-amber brown color fruit, having medium yellow flesh with a yellow pit well. The fruit is symmetrical and round, juicy, has good eating, keeping and shipping qualities and is suitable for fresh market.

1 Drawing Sheet

This invention relates to a new and distinct variety of peach tree having good keeping and shipping qualities and being useful for fresh market.

The new variety was discovered in 1978 by Paul Chapus in his orchard of Springcrest variety peaches in St-Laurent-du-Pape, France. The new variety was found as a mutation on a branch of a Springcrest peach tree.

The new variety, given the varietal name Starcrest, was reproduced asexually by Hubert Veauvy. The reproduction was accomplished by taking budwood from the mother tree and grafting the budwood in 1981/1982. These trees exhibit the same characteristics as the mother tree. A second series of grafts were made in 1982/1983. The second series of trees also exhibit the same characteristics as the mother tree. The asexual reproduction has taken place at various testing sites in France.

The FIGURE illustrates two external views of the fruit of the new variety, a longitudinal section of the fruit of the new variety showing the pit embedded in one half, and two leaves of the new variety.

PLANT CHARACTERISTICS

The new variety is of medium size and has medium vigor. The shape of the tree is upright with the shape and density determined by pruning. The new variety is moderately productive, bearing regularly. The trunk diameter, in relation to its length, is 60 cm to 360 cm. The trunk is medium-stout, with a moderately rough, brown bark. The branches are medium in size with good angle insertion and moderately rough bark. The color of the branches ranges from brown to reddish-brown. The branches have numerous lenticles. The lenticles are medium in size and are rather pronounced, with raised lips.

The leaves are medium in size, having lengths of about 18 cm and widths of about 3.9 cm. They are green in color with an elliptic lanceolate. The form of the margin is crenate, while the glandular characteristic is globose. The petiole is very short, having a length of 0.5 cm and being moderately thick. The stem glands number two and are arranged with one on each side of the stem insert and head of the petiole. The stem glands are small globose and are green-reddish in color. The leaves have stipules.

The characteristics of the flower are substantially the same as those of the Maycrest peach variety.

The fruit matures about 15 days before the Springcrest peach and 5 days before the Springold peach. The fruit ranges in diameter from 56 to 61 mm and has an average weight of 85–105 gms. The transverse length in suture plane in 61 mm while the transverse length at right angles to the suture plane is also 61 mm. The form of the fruit is globose and is quite regular. It is symmetrical, round and regular. The suture is nearly a line and is medium in size, the position of the suture being not at all creased in the cavity.

The stem cavity is of medium depth with the apex being rounded, usually sloping slightly ventrally. The stem has a length of about 1 cm and width of about 0.15 cm. The skin is of medium thickness and exhibits no tendency to crack. The skin color is a bright red blush or striped red on yellow-amber brown color. Its pubescence is fine and short.

The flesh is medium yellow in color. The color of the pit well is yellow. The fruit is juicy with good flavor, medium aroma and medium texture. The fibers are firm but melting. The fruit has good eating qualities. The stone is semi-free, having a size of 29×22 mm with a thickness of 14 mm. The shape of the stone is elliptic to ovate and is brown in color. The base of the stone slopes somewhat toward the ventral suture. The grooves in the stone are deep, with the dorsal edge more or less rounded and the ventral edge rather deeply grooved from base to apex. The stone has no tendency to split.

The use of the fruit is intended to be fresh market and has good keeping and shipping qualities. The resistance to disease of the variety in unknown.

We claim:

1. A new and distinct variety of peach tree as described, illustrated and identified by the characteristics enumerated above, the fruit of which is juicy with a medium aroma, has a medium yellow color, provides good eating, keeping and shipping qualities and is useful for fresh market.

* * * * *

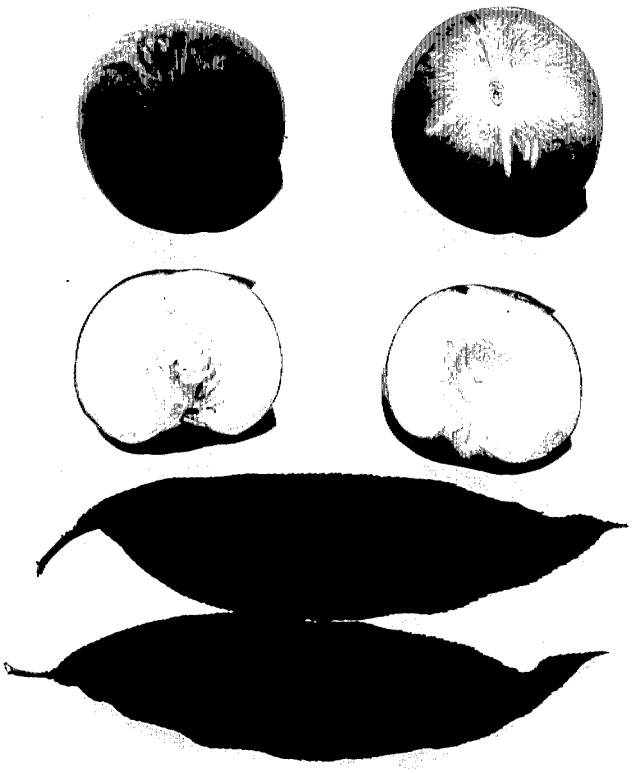
FIGURE